United States Patent
Sachs et al.

(10) Patent No.: US 9,962,166 B1
(45) Date of Patent: May 8, 2018

(54) METHOD AND APPARATUS FOR PERFORMING A SURGICAL OPERATION ON THE CERVICAL PORTION OF THE SPINE

(76) Inventors: David P. Sachs, Boca Raton, FL (US); Robert E. Simonson, Boca Raton, FL (US)

(*) Notice: Subject to any disclaimer, the term of this patent is extended or adjusted under 35 U.S.C. 154(b) by 1129 days.

(21) Appl. No.: 12/069,654

(22) Filed: Feb. 12, 2008

(51) Int. Cl.
*A61F 2/46* (2006.01)
*A61B 17/15* (2006.01)

(52) U.S. Cl.
CPC .................. *A61B 17/155* (2013.01)

(58) Field of Classification Search
USPC ...... 606/279, 86 R, 79–85; 623/17.11–17.15
See application file for complete search history.

(56) References Cited

U.S. PATENT DOCUMENTS

| | | | |
|---|---|---|---|
| 4,341,206 A | 7/1982 | Perrett et al. | |
| 5,015,247 A | 5/1991 | Michelson | |
| 5,180,382 A | 1/1993 | Frigg et al. | |
| 5,246,458 A | 9/1993 | Graham | |
| 5,324,290 A | 6/1994 | Zdeblick | |
| 5,364,399 A | 11/1994 | Lowery et al. | |
| 5,549,612 A | 8/1996 | Yapp | |
| 5,591,235 A * | 1/1997 | Kuslich | 606/261 |
| 6,436,102 B1 * | 8/2002 | Ralph et al. | 606/90 |
| 6,679,886 B2 | 1/2004 | Weikel et al. | |
| 7,094,239 B1 | 8/2006 | Michelson | |
| 7,128,760 B2 | 10/2006 | Michelson | |
| 7,160,304 B2 | 1/2007 | Michelson | |
| 2003/0065396 A1 * | 4/2003 | Michelson | 623/17.15 |
| 2003/0125747 A1 * | 7/2003 | Sproul | 606/92 |
| 2003/0181982 A1 * | 9/2003 | Kuslich | 623/17.16 |
| 2003/0195518 A1 * | 10/2003 | Cragg | 606/80 |
| 2006/0111714 A1 * | 5/2006 | Foley | 606/61 |
| 2009/0076555 A1 | 3/2009 | Lowry et al. | |

OTHER PUBLICATIONS

Europine Spine Journal, Jan. 3, 2007, Gun Choi et al.

* cited by examiner

*Primary Examiner* — David Isabella
*Assistant Examiner* — Christine Nelson
(74) *Attorney, Agent, or Firm* — Burr & Forman LLP; Jeffrey H. Kamenetsky (57) ABSTRACT

This invention is the method of treating an ailment associated with the cervical portion of the spine by performing an intravertebral corpectomy that includes the steps of removing the vertebral corpus to define a working channel for the surgeon to gain access to the epidural space so as to attend to and perform a procedure on the pathology. This method obviates the problems incidental to more radical cervical spine operations such as discectomy or corpectomy which requires removal of a portion of the vertebra and adjacent intervertebral discs for decompression of the cervical spinal cord and spinal nerves and using a bone graft with or without a metal plate and screws to reconstruct the spine and provide stability. Prior to terminating the surgery, the opening formed by the removed vertebral corpus is fitted and/or filled with a suitable implant.

11 Claims, 6 Drawing Sheets

METHOD AND APPARATUS FOR PERFORMING A SURGICAL OPERATION ON THE CERVICAL PORTION OF THE SPINE

RELATED APPLICATIONS

Not applicable

FEDERALLY SPONSORED RESEARCH OR DEVELOPMENT

Not applicable

TECHNICAL FIELD

This invention relates to the method of performing a surgical procedure to alleviate problems associated with the cervical spine and cervical vertebrae and cervical intervertebral discs and more particularly, to perform an intravertebral corpectomy as will be described in detail herein below. The invention also relates to implants associated with the after portion of the intravertebral corpectomy procedure.

BACKGROUND OF THE INVENTION

The current state of spine surgery teaches the technique of radical intervertebral discectomy for the purpose of providing surgical access to a pathology posterior to the disc space and or vertebral body (sometimes referred to as vertebral corpus) and anterior to the spinal cord and/or nerve roots. Removal of the spinal disc (discectomy) generally requires the final step of fusing the adjacent vertebral bodies or placing an artificial disc where the patient's natural disc previously existed. Both of these final steps to the disc removal techniques are accompanied by loss of mobility, compromises to the patient's future, and the possibility of additional surgeries. It is important to point out that the current state of spine surgery requires the radical removal of two spinal discs in the performance of a single level standard corpectomy, thus requiring multilevel fusion with permanent loss of motion at two levels of the spine. What is being emphasized is the fact that following the discectomy or corpectomy procedures the affected area of the patient needs to be reconstructed which typically requires a spinal fusion. One aspect of this invention is that the procedure that will be described herein below completely eliminates the necessity of performing a spinal fusion and in addition, the implant that is utilized in this procedure is not for the purpose of the fusion of two vertebral bodies but more importantly, it is for the purpose of restoring the bone that is used in performing the inventive procedure back to its functional condition.

The spinal disc is made up of a durable exterior called the annulus fibrosis and the soft cushioning interior called the nucleus pulpous. The spinal disc along with bony supports called facets at the posterior aspect of the spine and the ligamentous structures make up the vertebral motion segment or joint. These motion segments provide support and structural stability for the body and provide the patient with normal flexibility and the anatomically correct distribution of the biomechanical loads required of the human body.

Historically, anterior spinal surgery has been performed by gaining access to the spinal nervous anatomy and pathology by creating pathways through an intervertebral disc (discectomy) or by removing two or more intervertebral discs and one or more vertebral bodies. These techniques have required intervertebral surgical fusion at one or more levels to reconstruct the spine eliminating one or more vertebral motion segments. Recently, the performance of radical discectomy in conjunction with implantation of a total artificial disc replacement has been advocated as a means of performing anterior decompression surgery without spinal fusion. Described and disclosed here is a new method of gaining surgical access that includes a step of repairably performing intravertebral corpectomy for a vertebral body while leaving the vertebral endplates, the lateral vertebral walls, and the intervertebral disc substantially intact and which avoids an intervertebral fusion or artificial disc replacement. This newly disclosed method of operation is in stark contrast to the current state of the art of the radical corpectomy/discectomy approach which is in common use today and has been for decades for multilevel or single level decompressive surgeries in which both soft tissue and bony pathology (anatomy) have been removed in such a way to result in the need for a single or multilevel fusion surgery. The corpectomy of today, prior to this disclosure, involves the irreparable removal of the vertebral body and the vertebral endplates and intervertebral discs above and below the corpectomy. The corpectomy approach in the cervical spine includes the step of placing a bone graft and eliminating the vertebral motion segments by fusing the levels undergoing surgery similar to any of today's common disc removal and fusion techniques. The unique steps of this newly disclosed procedure will, in contrast to previous and current techniques, preserve the motion segments, also referred to as a joint, made up primarily of an intervertebral disc and ligamentous structures and leave the joint in a primarily natural state. Stated directly and clearly this disclosed technique will not fuse, eliminate, or artificially attempt to mechanically replace a patient's otherwise viable joint.

Using the current state of the art, after the surgical removal of the intervertebral disc or intervertebral discs and vertebral body, the surgeon has now gained access to the region posterior to the intervertebral disc and vertebral body and access to the epidural space and may then proceed to use normally available surgical instruments to remove any tissue which is compressing the neural elements. The impact of the typical herniation, bone spur or other pathology on the patient's life is enormous, but the actual size of the tissues needing to be removed from the cervical spine is often only a few millimeters in length.

Once the pathology has been removed the surgeon must now move on to the step of reconstructing the spine where the surgically created cavity was created during the step of exposing the pathology by removing the intervertebral disc or intervertebral discs and vertebral body. This is most commonly addressed by the surgeon performing an intervertebral fusion. This type of spinal fusion is generally augmented with a stabilization procedure that utilizes a titanium plate on the anterior aspect of the spine which is affixed to the vertebral bodies above and below the location of the decompressive surgery with titanium screws.

Bone heals best after the hard exterior shell known as the cortical layer or cortical bone has been removed revealing the softer cancellous bone within the vertebral body. For this reason the surgeon usually begins the reconstruction of the surgically created spinal defect by using a high speed drilling instrument to carve away the hard cortical layer that makes up the vertebral endplates. Once bleeding cancellous bone has been exposed on the vertebral level above and below the removed disc or discs the surgeon may begin the step of preparing an implant.

Commonly used implants that help in promoting fusion are allograft bone, autograft bone and various manufactured devices including cages. Allograft is donated bone and autograft is bone taken from the patient. Allograft is usually provided from one of the nation's tissue banks and is cut from one of the bones of a cadaver specimen that has been designated as an organ donor. To meet the standards of an organ donor, the donor must have led a lifestyle deemed to not have a likelihood of transmitting disease and the cause of death must have been determined to not affect the bones.

Some surgeons feel donor bone does not heal as well as autograft bone. Also, some patients are uncomfortable with the idea of placing the bones of a deceased person into their bodies. For these reasons among others, surgeons will sometimes harvest a portion of a bone from the patient having spine surgery. The step of harvesting bone from a patient requires a separate simultaneous surgery on another area of the body to remove healthy bone. Many patients have reported that the harvesting of healthy bone from their bodies creates as much or more short, medium, and long term pain as the spinal surgery itself causes.

The next surgical step is to cut or machine the bone selected by the patient and surgeon to be used as an implant into a shape and size similar to the void created in the steps of removing the intervertebral disc or intervertebral discs and vertebral body and cutting away the adjoining vertebral endplates' cortical shells.

This shaping step is done in the operating room, usually by the attending surgeon using grinding or cutting tools. This is a critical step in the rebuilding process as an implant too deep could compress and injure the spinal cord. If the implant is too short it will not have proper contact with the bleeding cortical bone and will have undo motion not allowing for proper healing (union or fusion) which will likely prompt additional surgeries to repair the non union. If an implant is too tall, the spine can be over distracted potentially resulting in pain and structural instability. The combination of the intraoperatively shaped and cut vertebral cortical endplates and the custom formed bone implant are often referred to as parts of a construct.

In an additional effort to avoid post operative deformation of the spine and in a step to decrease the chances of the bone implant migrating to an undesirable location as well as for other reasons, another implant is usually added to the construct. This implant is typically called a cervical plate.

A cervical plate is most often made of titanium and is accompanied by screws of the same material. This plate is affixed to the anterior aspect of the spine by placing screws through the plate and into the vertebrae above and below the surgically created defect. Sometimes after the patient heals, another surgery is performed to remove the plate. Post operative complications including screw breakage, screw back out, screw displacement, plate breakage, plate migration, and other complications, can necessitate the removal of the spinal instrumentation. Other times the patient is reluctant to undergo additional surgeries and the plate is left in place.

The disadvantages of the removal of the intervertebral disc or intervertebral discs and vertebral body, and the following intervertebral fusion, by the placement of intervertebral fusion devices are many. Several of these disadvantages can lead to additional surgeries. A fused vertebral motion segment eliminates any movement the patient had previously at that level. This elimination of movement can lead to sore muscles, a reduction in normal activities and additional loading at the adjacent vertebral levels. This additional loading can cause adjacent intervertebral discs to prematurely collapse or wear out. The collapse of adjacent levels can require additional spinal fusions at those now affected levels.

The risk of adjacent level disc disease is great enough that often times a surgeon will suggest going ahead and fusing several levels of the spine during the first surgery if some of the adjacent levels look questionable, as it is possible that the adjacent asymptomatic levels will become symptomatic under the new postoperative conditions.

These costs, risks and unintended consequences are common enough and are thoroughly recognized to the point that many attempts have been made to find substitutes to the fusion procedure.

One of the latest attempts and possibly the most expensive is the artificial disc. Several companies have introduced or conducted clinical trials on various designs of artificial discs. Some are experimenting with augmenting or supplementing the disc, others are experimenting and trialing various designs of partial or complete artificial discs.

The placement of an artificial disc still requires the complete removal of the intervertebral disc to gain access to the surgical target. With the intervertebral disc removed a normal biologically and anatomically intact vertebral joint or motion segment postoperatively is not possible.

Artificial discs have only been available clinically for a short time and many of the pending designs are not yet complete. Therefore, the long term outcomes and potential problems with these devices are still an unknown. Some experts feel the artificial disc or supplemented disc will provide at a minimum an alternative to the definitive and generally considered non beneficial intervertebral union or fusion. Many of those experts also feel the likely result will be additional surgeries down the road for the patient as the artificial discs and or augmented discs wear out. Others also state that the changes provided by the artificial disc will alter the anatomical loading of the posterior facet joints leading to arthritis.

In accordance with this invention, after the surgeon has performed an incision in the skin of the patient in proximity to the pathology, the surgeon will next remove either mechanically with the use of a high speed bone dissecting instrument or by other means, such as using a laser or other instrument, the corpous portion of the vertebrae leaving but a shell defined by the lateral walls and end plates of the bone. The portion of the bone being removed preferably is beginning anteriorly or anterolaterally and extending inwardly toward the anterior or anterolateral epidural space and proximal to the dura.

The opening associated with this intravertebral corpectomy serves two alternate purposes. 1) The removal of the bone if in proximity to the pathology can in the process of removal also remove the pathology, or 2) it provides a space that allows the surgeon to perform a surgical procedure that is directed to remove the pathology or treat the surgical target. In either process, the intravertebral corpectomy allows the procedure for removing or treating the pathology without the necessity of providing an intervertebral fusion. Obviously, the elimination of the fusion, provides to the patient the mobility that was evidenced before the operation occurred. Hence, the intravertebral corpectomy affords a medical procedure that obviates the fusion required when other types of medical procedures, like discectomy or cervical corpectomy, are performed.

SUMMARY OF THE INVENTION

An object of this invention is to provide an improved method of treating a pathology on the cervical or other portion of the spine by performing the intravertebral corpectomy method.

A feature of the intravertebral corpectomy for treating pathology in the cervical portion of the spine is the step of removing a portion of the intravertebral corpus for providing a working channel for the surgeon to perform a procedure directed toward the pathology.

The foregoing and other features of the present invention will become more apparent from the following description and accompanying drawings

DETAILED DESCRIPTION OF THE INVENTION

The following description details the method of this invention outlining the procedure a surgeon will follow using the intravertebral corpectomy. The patient is prepared for surgery using generally accepted operating procedures normally practiced for spine surgery, and once anesthetized in a traditional manner, the patient is suitably supported for the spine procedure. As used herein the term pathology means any form of medical impediment requiring surgical intervention.

Figure 6:
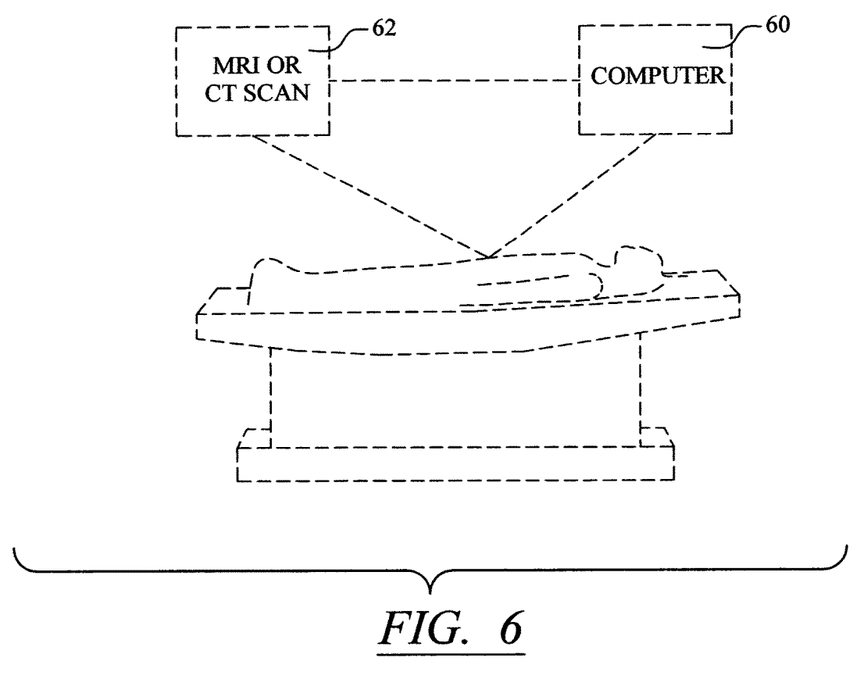
FIG. 6 is a schematic illustration of an MRI or CT Scan connected to a computer for generating a phantom.

A transverse incision centered over the medial border of the sternocleidomastoid muscle is performed. Bleeders in the skin edges are coagulated with bipolar cautery. The platysma is divided in the direction of the skin incision. Dissection is performed in the soft tissue plane medial to the sternomastoid muscle and the carotid artery and lateral to the trachea and the esophagus. The prevertebral fascia is identified. Deeper exposure is achieved using standard surgical retraction. Preoperatively, a phantom form of the patient's cervical spine is created upon a commercially available powerful computer as schematically illustrated in FIG. 6. This model will later be used intraoperativly as part of an image guidance system. The preoperative three dimensional phantom model is created utilizing the computer upon which an MRI and or a CT scan from a commercially available MRI or CT scanning instrument has been uploaded which allow the creation of the accurate three dimensional model. Obviously, other imaging technologies such as fluroroscopy or other imaging modalities, such as the O-arm™ Imaging System available from Breakaway Imaging, LLC, Littleton, Mass., can be used without departing from the scope of this invention. Using the phantom model of the individual patient's spine, the volume of dissection and the geometric shape of the intravertebral corpectomy as well as the trajectory of the surgery to be performed are planned. Using the phantom computer model with the planned trajectory, the surgeon has the opportunity with great detail to explore and validate the planned surgery in virtual reality prior to making an incision upon the patient.

After intraoperatively achieving satisfactory exposure of the anterior aspect of the cervical spine and after localizing and registering the correct level of surgery of the spine the intravertebral corpectomy is performed. The intravertebral corpectomy volume, geometric shape, and trajectory are performed according the preoperative plan created prior to the step of incising the patient. In some instances it may be preferred to acquire imaging data and computer planning after the incision has been made. Several bone dissecting instruments could be used at this point to remove the intravertebral corpus in a manner which will terminate upon the disc material and osteophyte (combined pathology, using a common pathology as an example) requiring removal. To promote the accuracy of the bone dissection intraoperative image guidance will be used in conjunction with the bone dissection instruments in order to follow the preoperative plan developed upon the virtual reality model. The removal of the disc material and osteophyte pressing on the spinal cord and/or nerves as well as the performance of the intravertebral corpectomy will adequately decompress the neural elements, thus curing the pathology and reliving the patient's symptoms. The removal of only the portion of the disc which has herniated and the associated focal osteopyte with the carefully calculated volume and trajectory of the intravertebral corpectomy will allow the treatment of the disease and permit the surgery to terminate without the fusion of two vertebral bodies together into one larger bone mass. In addition, this technique obviates the need to place an implant in the disc space or to place an anterior cervical plate.

Figure 1:
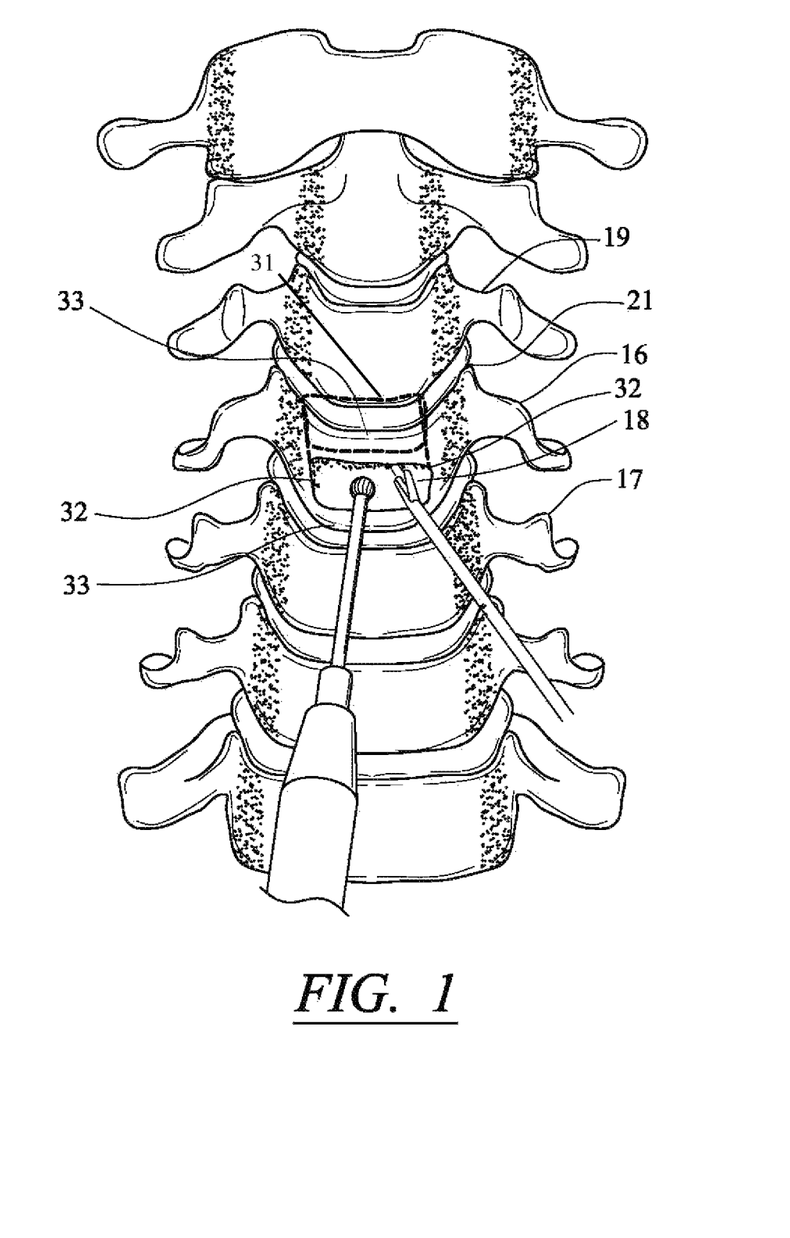
FIG. 1 is a rendition of the seven vertebrae forming the cervical portion of the spine of a human including the atlas, axis and five additional vertebrae with a schematic showing of a working channel formed by the removal of the intravertebral corpus.
Figure 2A:
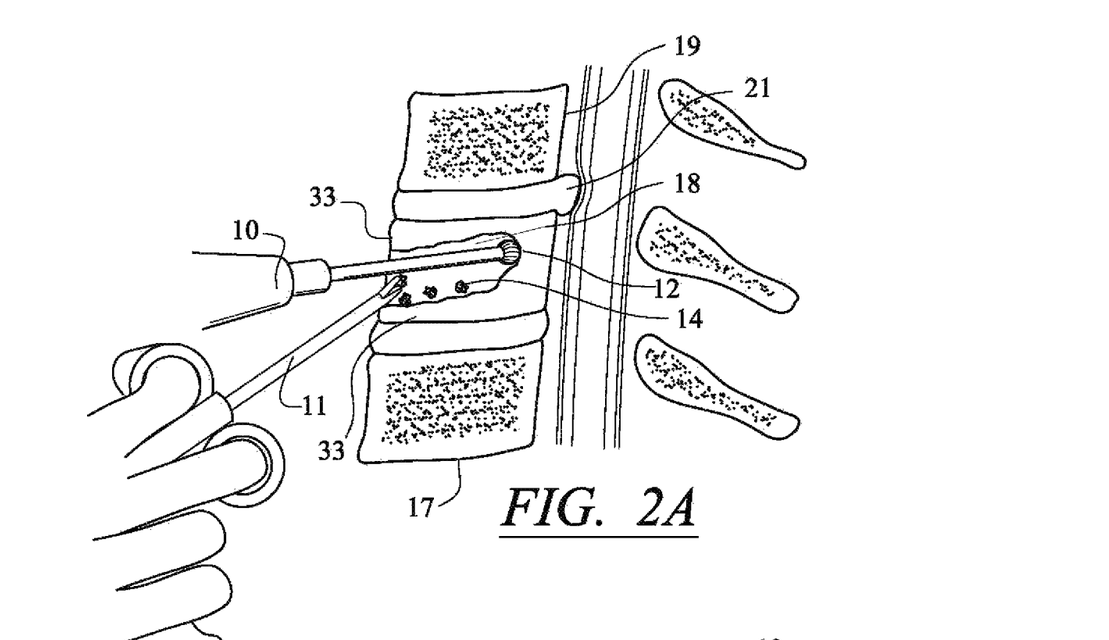
FIG. 2A is a fragmentary and cutaway view of the intravertebral corpus illustrating a high speed bone dissecting burr removing a portion of the removed corpus of the vertebrae leaving but a shell defined by the lateral walls and end plates of the bone.
Figure 2B:
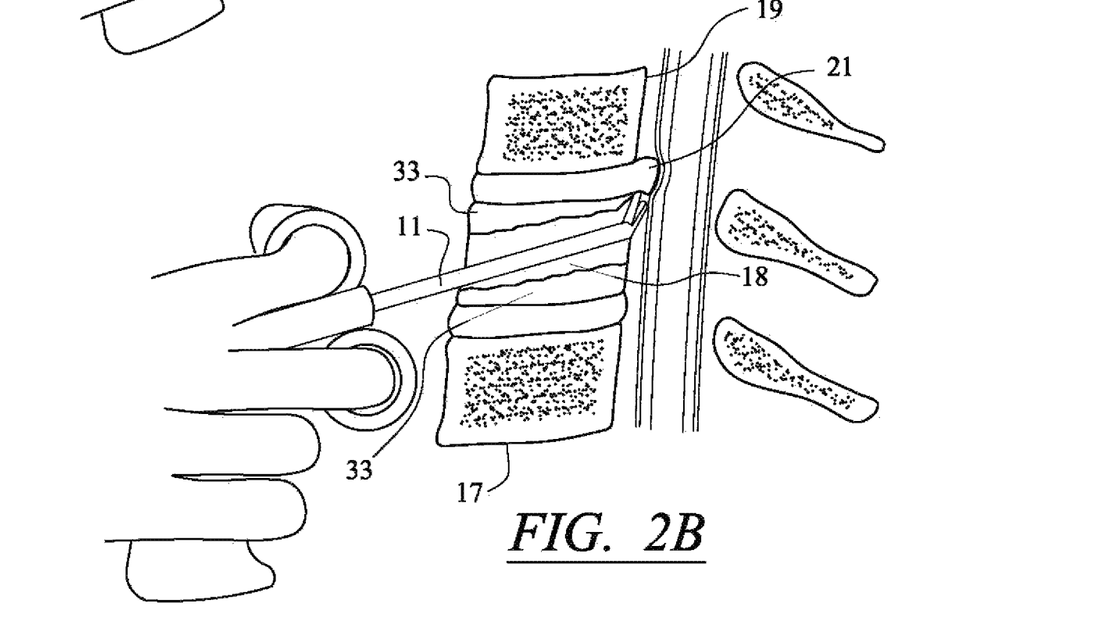
FIG. 2B is a cutaway view of a portion of the spine identical to the view depicted in FIG. 2A illustrating the vertebral corpus being removed to extend to the dura and a hand held surgical tool being operated to remove the pathology.
Figure 2C:
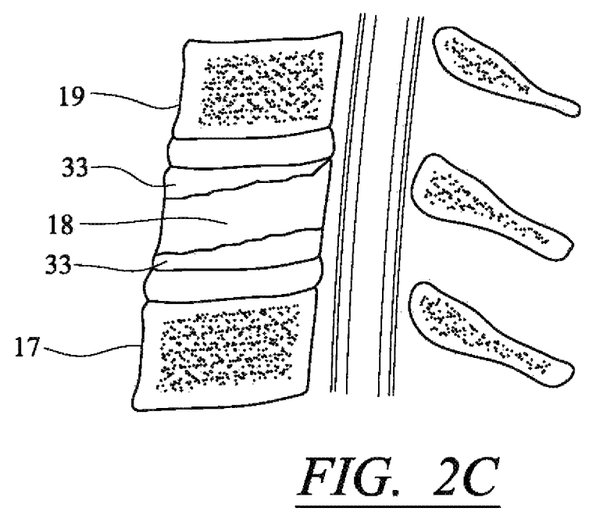
FIG. 2C is a cutaway view of the portion of the spine identical to the view depicted in FIG. 2B illustrating the condition of the vertebrae after the pathology has been removed.
Figure 2D:
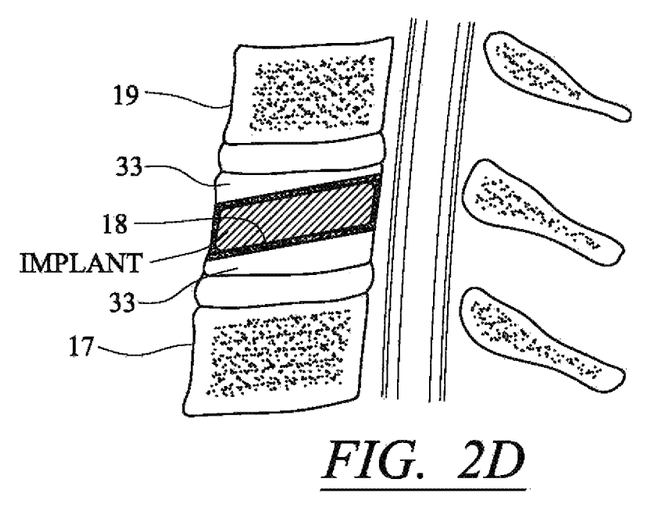
FIG. 2D is a cutaway view of the vertebrae depicted in FIG. 2C with an implant planted in the void made in the vertebral corpus.

As best seen from FIGS. 1-2D the intravertebral corpectomy is shown step by step as an example as it is applied to a particular pathology wherein a high speed bone dissecting instrument partially shown as reference numeral 10 includes a burr 12 for removing the vertebral corpus or body 14 of the vertebrae 16 spaced between the two adjacent vertebrae 17 and 19. As shown in FIG. 1, the surgeon forms a channel 18 in the vertebrae 16 that is sufficiently opened to allow the passage of the several operating tools that are used to perform the surgery and remove the pathology and provide sufficient visualization of the target. FIG. 1 also illustrates channel 18 created within vertebra 16. Vertebra 16 includes a corpus portion (not shown in FIG. 1), lateral vertebral walls 32, and vertebral endplates 33. Channel 18 is created by removing the corpus portion of vertebra 16 leaving a shell 31. Shell 31 is defined by lateral vertebral walls 32 and vertebral endplates 33. FIG. 2A illustrates tool 11 in the process of removing the corpus portion 14 from vertebra 16. FIG. 2B illustrates the surgeon removing a portion of a bulging disc 21 with the use of a grasping instrument 11 passing through the surgeon made channel 18 into the greater epidural space offering the surgeon sufficient m to manipulate the surgical tool. FIG. 2B illustrates vertebra 16 after the removal of the vertebral corpus 14 (not shown in FIG. 2B), leaving endplates 33 functionally intact. The channel 18 and the post operative condition of the vertebrae is shown in FIG. 2C and it being noted that the two adjacent vertebrae are left intact and that the intravertebral corpectomy may allow the treatment of the disease and permit the surgery to terminate without the fusion of two vertebral bodies together into one larger bone mass. FIG. 2D illustrates the implant placed into avoid created by the removal of the vertebral corpus 14. In addition, this technique obviates the need to place an implant in the disc space or to place an anterior cervical plate. In some instances the two vertebral bodies may not be fused together and a particular type of implant placed between the two vertebral bodies. As is well known the surgery or portions thereof can be assisted with the use of well known robotics, either of the types that are hand controlled or electronically controlled, as for example, the commercially available da vinci surgical system manufactured by Intuitive Surgical, Inc. of Sunnyvale, Calif.

After the decompression of the spine as described above, the surgeon may choose an implant to be placed into the cavity created in the step of the intravertebral corpectomy. To aid in the implant selection process, several implant trial instruments will be available. With the size and shape of the implant selected, the surgeon will then prepare the remaining portion of the vertebral shell by cutting/tapping a thread or form into the remaining bone. The term implant trial instruments as used herein is a well accepted terminology in the medical technology and refers to plugs that are at given sizes and shapes that are used by the surgeon to determine the size and shape of the implant that will be used to fill the void.

After the step of cutting a thread or form into the bone and selecting an implant, the implant will be packed with a demineralized bone matrix material, a selected osteoconductive material or other material of the surgeon's choosing, and then securely screwed or impacted into the intravertebral corpectomy space.

Figure 3:
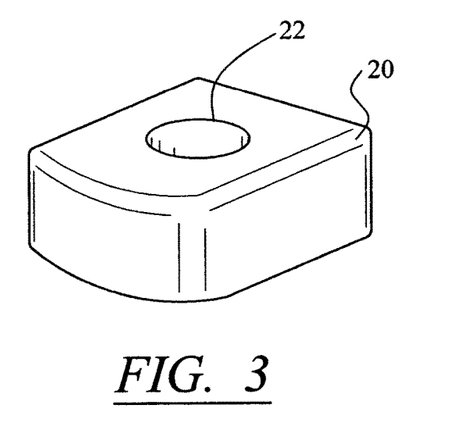
FIG. 3 is a view in perspective illustrating a polygonal shaped implant designed it fit into the core of the opening formed in the vertebrae.
Figure 4:
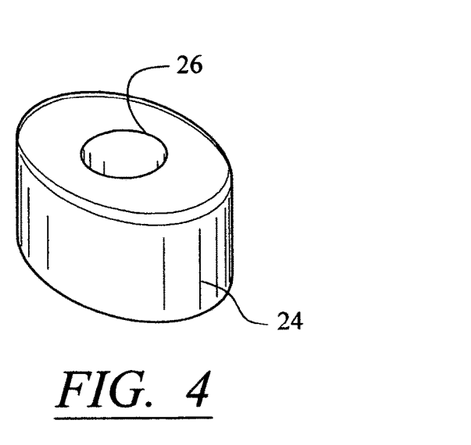
FIG. 4 is a view in perspective illustrating a cylindrical ovoidally shaped implant designed to fit into the core of the opening formed in the vertebrae.
Figure 5:
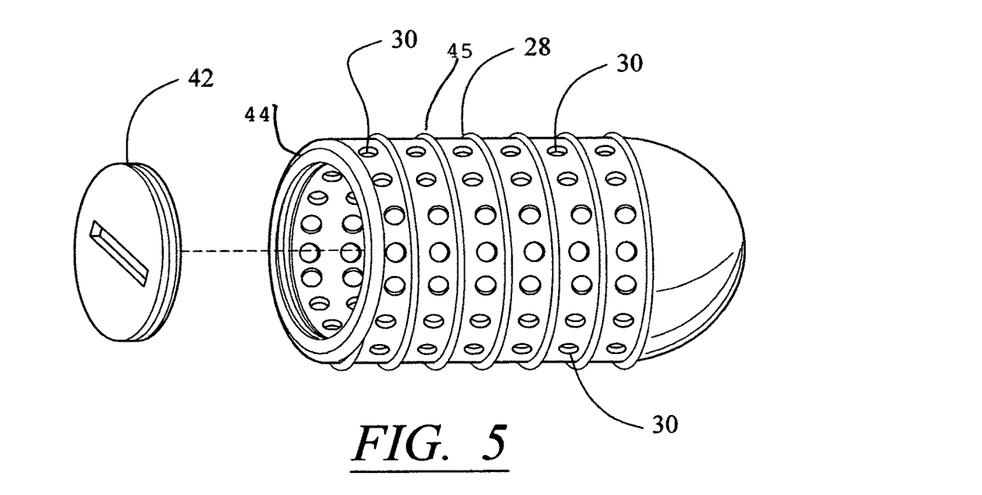
FIG. 5 is an exploded view with another embodiment of a conically/cylindrically shaped implant with a top cover designed to fit into the core of the opening formed in the vertebrae.

With the intravertebral corpectomy, neural decompression and vertebral body reconstruction completed, final imaging is performed to confirm accurate placement of the intravertebral implant. Closure of the incision is performed in the standard fashion and the surgery is concluded. FIGS. 3, 4 and 5 illustrate examples of the types of implants that would be utilized in filling the vertebral corpus following the treatment of the pathology. The shape of implant 20 is polygonal having a circular recess 22 formed in the center thereof. The shape of implant 24 is cylindrical and also includes a central recess 26. Implant 28 is a hollow bullet shaped body most of which is uniform in size and includes a plurality of radial holes 30 extending into the inside thereof. A removable cap 42 serves to cover the top end 44 of implant 28 and the implant includes helically wound threads 45 on the periphery thereof Inner threads at the top end thereof serve to threadably accept the removable cap 42. After the surgeon has obtained the proper size of the channel by using suitable and well known measuring instruments, the surgeon will tap the inner surface of the vertebral corpus to match the threads 45 of the implant intended to be used so that the surgeon can then thread the implant in place. The material selected for the implant is characterized as material that promotes bone in-growth, is compatible with bone growth, or may be used with bone growth promoters such as commercially available bone morphogenic protein (BMP), for example. The method of inserting an implant is described herein below.

The implant, as the one shown in the implant depicted as reference numeral 28, comprises a cylindrical member having an outside diameter larger than the void in a vertebrae to be filled. A series of threads on the exterior of the cylindrical member engages threads formed in said void to maintain said implant in place. As shown the implant includes a plurality of openings in the cylindrical surface thereof and the outside diameter of said cylindrical member being substantially uniform over the entire length of the implant. The implant has a hollow portion for receiving bone graft materials for promoting bone in-growth, a removable cap covering the hollow portion and threads in the cap for screwing onto the hollow portion. In order to insert or remove the implant from the void, this invention contemplates the use of surgical insertion and removal instruments.

FIG. 6 schematically illustrates the process for obtaining the three dimensional phantom model with the use of a well known and commercially available computer shown as a blank box 60 upon which an MRI and or a CT scan from a commercially available MRI or CT scanning instrument shown as blank box 62. The patient is exposed to these instruments in a well known method.

Figure 7:
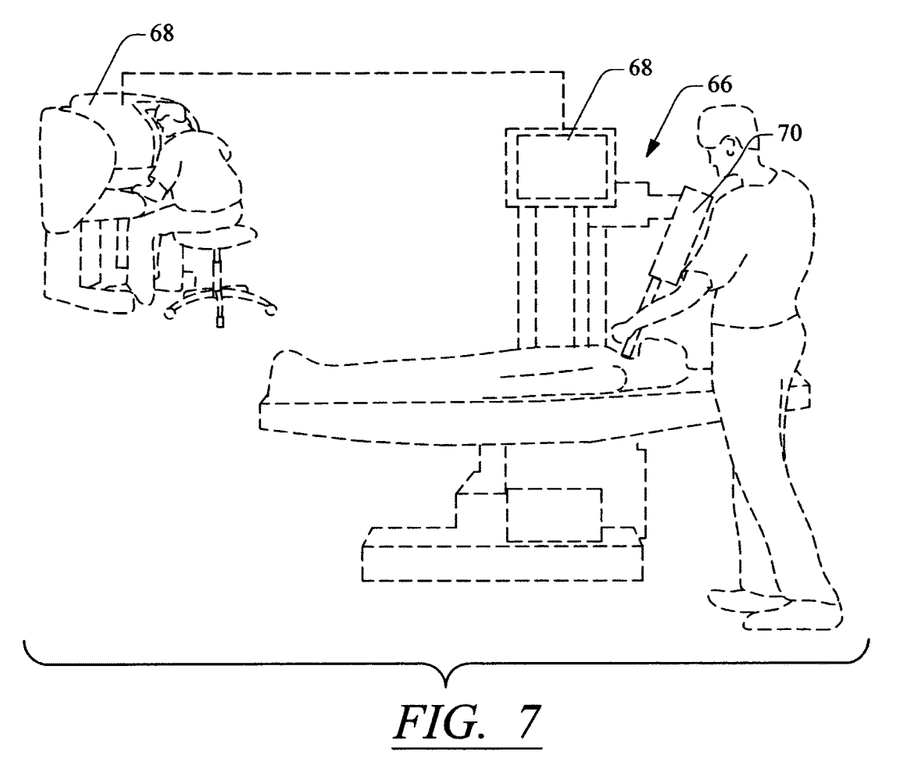
FIG. 7 is a schematic illustration of a patient being operated on by a surgeon with the use of robotics.

FIG. 7 schematically illustrates a well known commercially available robotic apparatus generally illustrated by reference numeral 66 that includes the control 68 that response to the remote electronic console 68 being suitably operated by a qualified operator and providing movement of the arm 70 that carries the instrument used in the particular procedure used to treat the pathology.

What has been shown by this invention is a new technique that is applicable to treating pathology on the cervical portion of the spine and this method of operation avoids some to the drastic techniques that have been employed in the past. The performance of this technique removes a portion of the corpus of the vertebrae to open a channel to allow the surgeon to gain access to the pathology, in what is described in this patent application as an intravertebral corpectomy, so as to allow the treatment of the disease and permit the surgery to terminate without the fusion of two vertebral bodies together into one larger bone mass. And further, to obviate the need to place an implant in the disc space or to place an anterior cervical plate. Owing to this technique, the surgeon now has available at his discretion several options of filling the void with various types of implants which serve to return the vertebrae to its functional condition. This type of implant has to be distinguished from the heretofore used implants that merely serve to occupy the space left opened by the removed disc.

Although this invention has been shown and described with respect to detailed embodiments thereof, it will be appreciated and understood by those skilled in the art that various changes in form and detail thereof may be made without departing from the spirit and scope of the disclosed invention.

We claim:

1. A method of performing an intravertebral corpectomy for surgically treating pathological tissue, the method comprising creating a working channel in a vertebra, the vertebra including a corpus portion, lateral vertebral walls and vertebral endplates, the working channel created by removing the corpus portion of the vertebra leaving a shell, the shell defined by the lateral vertebral walls and the vertebral endplates, while leaving the lateral vertebral walls and the vertebral endplates and intervertebral discs functionally intact thereby avoiding intervertebral fusion of adjacent vertebrae;

performing the surgery through the working channel to treat the pathological tissue; and placing an implant into a void created by the removal of the corpus portion.

2. The method of claim 1, further including treating the pathological tissue at a location posterior to the vertebra.

3. The method of claim 1, further including accessing a greater epidural space by way of a space formed by creating the working channel.

4. The method of claim 1, wherein the implant is configured to reconstruct the vertebra.

5. The method of claim 4, further comprising determining proper sizing of the implant.

6. The method of claim 4, wherein the implant is a threaded implant.

7. The method of claim 4, further including shaping the implant to reconstruct the vertebra.

8. The method of claim 1, further comprising: providing a series of implants; and selecting at least one implant from the series of implants to reconstruct the vertebra.

9. The method of claim 1, further comprising:

providing a plurality of implants for placement into a spinal defect, each of the plurality of implants having varying dimensions;

selecting at least one implant from the plurality of implants; and placing the selected at least one implant into the defect.

10. A method of performing an intravertebral corpectomy for anterior surgery to the spine for surgically treating pathological tissue, the method comprising:

creating a working channel in a vertebra, the vertebra including a corpus portion lateral vertebral walls and vertebral endplates, the working channel treated by removing the corpus portion of the vertebra leaving a shell, the shell defined by the lateral vertebral walls and the vertebral endplates, while leaving the lateral vertebral walls and the vertebral endplates and intervertebral discs functionally intact thereby avoiding intervertebral fusion of adjacent vertebrae; and placing an implant into a void created by the removal of the corpus portion.

11. A method of performing an intravertebral corpectomy for a surgery to the spine for surgically treating a pathological tissue, the method comprising:

creating a working channel in a vertebra, the vertebra including a corpus portion, lateral vertebral walls and vertebral endplates, the working channel created by removing the corpus portion of the vertebra leaving a shell, the shell defined by the lateral vertebral walls and the vertebral endplates, while leaving the lateral vertebral walls and the vertebral endplates and intervertebral discs functionally intact thereby avoiding intervertebral fusion of adjacent vertebrae, the removal of the corpus portion providing access to a location posterior to the vertebrae;

performing the surgery through the working channel to treat the pathological tissue; and placing an implant into a void created by the removal of the corpus portion.

* * * * *

UNITED STATES PATENT AND TRADEMARK OFFICE
CERTIFICATE OF CORRECTION

PATENT NO. : 9,962,166 B1
APPLICATION NO. : 12/069654
DATED : May 8, 2018
INVENTOR(S) : David P. Sachs and Robert E. Simonson Page 1 of 1

It is certified that error appears in the above-identified patent and that said Letters Patent is hereby corrected as shown below:

In Column 7, Line 7, replace the stand-alone letter "m" with "room";
In Column 7, Line 17, replace "avoid" with "a void";
In Claim 2, Column 9, Line 15, replace "vertebra" with "corpus portion";
In Claim 10, Column 10, Line 7, replace "treated" with "created";
In Claim 11, Column 10, Line 30, replace "vertebrae" with "corpus portion".

Signed and Sealed this
Thirteenth Day of November, 2018

Andrei Iancu
*Director of the United States Patent and Trademark Office*